United States Patent [19]

De Gasperi et al.

[11] 4,433,385
[45] Feb. 21, 1984

[54] METHOD AND APPARATUS FOR REAL TIME DETECTION OF FAULTS IN INDUSTRIAL OBJECTS

[75] Inventors: Mario M. De Gasperi, Milan; Antonio Racciu, Turin; Dario Nari, Barge, all of Italy

[73] Assignee: Tasco S.p.A., Milan, Italy

[21] Appl. No.: 224,665

[22] Filed: Jan. 13, 1981

[30] Foreign Application Priority Data

Jan. 14, 1980 [IT] Italy .............................. 19205 A/80

[51] Int. Cl.³ ............................................ G06F 15/46
[52] U.S. Cl. ................................... 364/554; 364/552; 364/507; 358/106
[58] Field of Search ............... 364/552, 554, 507, 468, 364/469, 812; 358/101, 106, 107, 93; 356/392–394; 250/572

[56] References Cited

U.S. PATENT DOCUMENTS

| 3,676,008 | 7/1972 | West et al. | 356/446 |
| 3,763,361 | 10/1973 | Smart | 364/554 |
| 3,876,872 | 4/1975 | Spitz | 364/554 |
| 3,908,118 | 9/1975 | Micka | 356/237 |
| 3,936,800 | 2/1976 | Ejiri et al. | 358/93 |
| 3,996,421 | 12/1976 | Pruznick et al. | 358/166 |
| 4,045,659 | 8/1977 | Akagawa et al. | 364/554 |
| 4,056,716 | 11/1977 | Baxter et al. | 358/106 |
| 4,139,779 | 2/1979 | Ehrat | 250/556 |
| 4,320,463 | 3/1982 | Himmelstein | 364/552 |

FOREIGN PATENT DOCUMENTS

54-133022 10/1979 Japan ................................ 358/106

OTHER PUBLICATIONS

"Tablet Checker", published in Fuji Electric Review, vol. 26, No. 1, 1980, pp. 20–24.
"Automated Photomask Inspection", by Novotny, published in Solid State Technology, vol. 21, No. 1, pp. 55–57, May 5, 1978.
"Traitement d'Images en Temps Reel pour la Detection des Defauts", Lelievre et al., Nouvel Automatisme, vol. 23, No. 11, Nov. 1978, pp. 342–345.
"Digital Image Processing by Use of Local Statistics", by Lee, published in Proceedings of the IEEE Computer Society on Pattern Recognition and Image Processing, May–Jun. 1978, pp. 55–61.

Primary Examiner—Gary Chin
Attorney, Agent, or Firm—Fidelman, Wolffe & Waldron

[57] ABSTRACT

Method and apparatus for the detection of faults in industrial objects and signalling such faults to handling apparatuses. According to the invention, the image is taken of a sample object by a television camera or other sensing device; the image is digitized and stored in a frame memory. The digitized sample (standard) image is then divided into small areas, for each of which the square root of variance (standard deviation) for the luminance levels of dots belonging to each area is calculated and stored. The same operations and elaborations are followed for each object to be checked and the obtained values are compared with those of the sample. When the differences thereof are above predetermined thresholds, an output signal is generated for distinguishing the fault and generally the faulty object and for controlling a handling apparatus for the objects.

11 Claims, 6 Drawing Figures

METHOD AND APPARATUS FOR REAL TIME DETECTION OF FAULTS IN INDUSTRIAL OBJECTS

This invention relates to a method and apparatus for industrial automatic quality control, i.e. for real time detection and signalling of faults in objects or industrial products, either two-dimensional or three-dimensional, uniform or decorated, single or multicoloured. We define as fault those visible differences between the object and a sample thereof which cause a quality degradation of said object.

Many studies, researches and devices using image processing methods have been proposed for the detection of faults, such as spots, points, scores, chipped edges, irregularity in shape or in any case differences in the object to be checked as compared with the sample thereof. We can distinguish three main trends in the image processing methods for the investigation of faults or anomalies in objects:

(1) Structural and formal analysis;
(2) Methods for image processing (e.g., use of Fourier transform);
(3) Arithmetic methods.

As a matter of fact, the first method mainly deals with linear shapes or two-dimensional geometries, such as in written character recognitions or in pattern making said planning.

The second method has been hitherto successful only in laboratory, as requiring on one hand great calculation powers and not being sufficient on the other hand for an automatic selection because of requiring a continuous operator's intervention; actually it aids in research, but can not be applied to industrial practice.

The third method does not solve at present the selection problem because of not taking into account all or at least some of the big problems that may be summarized as follows:

Illumination uniformity: although accurate and thoroughly studied, it is extremely difficult to be obtained; in theory, from the standpoint of a positive industrial application, it is almost impossible to assure a uniform illumination of the object throughout the field to be scanned. As a consequence, normally in any optical sensing system, each fault having a light intensity difference (measured by its reflectance) lower than the luminosity or brightness difference over the image field, though provided by very good illuminators (the best ones give differences not lower than 10%) may not be detected. As a matter of fact, besides providing illumination, the optical apparatus and detector (photodiodes, television tube, etc.) affect the illumination uniformity, often adding more differences. In fact, both do not have a homogeneous response throughout the field to be checked.

Detector Noise: every detector has its own noise, from the actual detection to the digital conversion that may be limited but not cut off; in this noise the differences between dot and dot that should be detected as faults, "drown". This problem adds to the former problem with similar effect.

"Noise" of the object to be checked: the surface of an object to be checked is never fully homogeneous. Rather, the surface has a "granularity" along with high local differences which may be greater, between dot and dot, than the faults to be detected. This effect is less visible to the eye in some objects having a great apparent homogeneity, such as a uniform, well made, print or a smoothed steel surface; on the other hand it is easier to detect this kind of noise in more coarse industrial objects which have a rough or painted surface.

However the problem is actually the same because in both cases one is looking for faults having visibility limits only slightly greater than the granularity of the object to be checked, however reduced this granularity is.

Drawing, edge and shape inaccuracies of the object to be checked: the systems, for instance for industrial decoration, are always affected by inaccuracies that depend on the production system itself.

In some cases, such as in xerography on tiles, silk or other objects, or in four-color process in a rotary machine, the inaccuracy with respect to the sample may be dramatic.

Similarly, the dimension and shape of the object reveal differences from the sample of generally reduced tolerances, but again larger than the faults to be found on the "edges".

The positive advantage of the method proposed by this invention is solution of these four problems in a completely automatic way, without the operator's intervention, and in real time, i.e., at such a speed that from 100 up to 200 objects per minute can be examined, according to the requirements of the production line.

Substantially, the method automatically provides the investigation process performed by human eye, that rejects and does not detect differences due to: a lack of illumination uniformity, noise of the object and inaccuracy of drawing and size. Rather, it integrates the collection information, and distinguishes those particular differences that are referred to as faults.

To better illustrate the characteristics of the method and apparatus that we claim, we will now refer to the selection of ceramic tiles according to the presence and degree of faults; it is however understood that the method and apparatus according to the invention may be used for the fault detection on any object or product, either bidimensional or tridimensional, or for the fault detection on any image, that is positive or negative photo, print reproduction or the like, for example on fabrics, metal plates and pieces, mechanical objects and the like.

The tiles referred to, and any other object or image to be checked may be composed of one or more colours, with regular or irregular drawings.

Hereinafter we will particularly describe the apparatus which, while used for multi-coloured objects, senses a black and white image: it being understood that the same apparatus, with the addition of two further sensors and suitable colour filters (e.g. a colour television camera) and the addition of as many systems for the conversion, storing and calculation, would sense the image of the object as resolved into its three basic colours and search for the faults thereof.

As a matter of fact the trichromatic detection is only a multiplication by three of the monochromatic apparatus and will not be described in the following because of its substantial identity.

The basic problem in selecting ceramic tiles arises in that during the various production steps (support, glazing and baking), differences may occur between the tile and its pattern, as visible to the nake eye, and degrading the quality of the tile, limiting its use in case of serious or high difference, and disrating it in case of slight difference. These differences or faults may, for instance, be very strong and small spots, less strong but wide spots, chipped edges, cracks, clefts, lack of glazing and the like.

At present, tiles are examined by skilled staff that, more or less quickly, divide them into first choice, inferior choices and scrap.

For the ceramic industry, the problem of the selection made by the operator is the personnel's high cost, the training cost and the non-homogeneous selection: for the personnel there is the problem of a monotonous and dull work, with scarce human contents and requiring a constant physical and intellectual attentiveness. The problem of inattention, namely removal for one moment of one's eyes from the point to be examined, is great as in all the visual inspections and, together with the different concentration capability, is the main cause of an incorrect classification of an object.

Therefore, it is an object of the present invention to provide a method and apparatus for the detection of faults in objects which the human eye, with eventually the aid of an optical instrument, considers visible; the classification of the objects according to the producer's demand; and the supply of suitable signals to a mechanical system dividing said objects into homogeneous groups as to quality thereof.

Generally, according to the claimed method, it is provided to effect the observation of the sample objects through a television camera or any other optical observing means, capable of outputting electrical signals (e.g. photodiode bar or phototodiode); this image is then converted from analog signals, to corresponding luminance levels; these signals are then divided and digitized according to a scale of luminance levels; these digital signals are then stored into a suitable frame memory, with biunivocal correspondance with the signals. The digitized image is then divided into small areas, for instance square areas, that in the embodiment to be described in the following comprise 16 dots (e.g. 4 for each side), but could vary according to applications, from areas comprising 4 dots (2 per side) to any other reasonable size that does not exceed, according to our experience, areas comprising 256 dots (16 per side).

In each of these areas the square root of the variance (standard deviation) is calculated according to the formula:

$$\sigma = \sqrt{\frac{\sum_{i=1}^{n} x_i^2}{n} - \frac{\left(\sum_{i=1}^{n} x_i\right)^2}{n^2}}$$

wherein
$\sigma$ = square root of variance (standard deviation) of the involved area;
$x_i$ = luminance value of the individual dots pertaining to the area;
n = number of dots contained in the area.

The $\sigma$ values of each area are stored as characteristic data of the comparison sample object.

The same method, through the same apparatus, is followed for each object to be compared and the $\sigma$ values for each area of said object are directly compared with the stored sample values.

The comparison values, which may be the difference between compared and predetermined thresholds, are then used by a calculating device for the production of a signal suitable to control mechanical selection and shunting apparatus.

The invention will now be described by way of example with reference to the accompanying drawings, in which.

Figure 1:
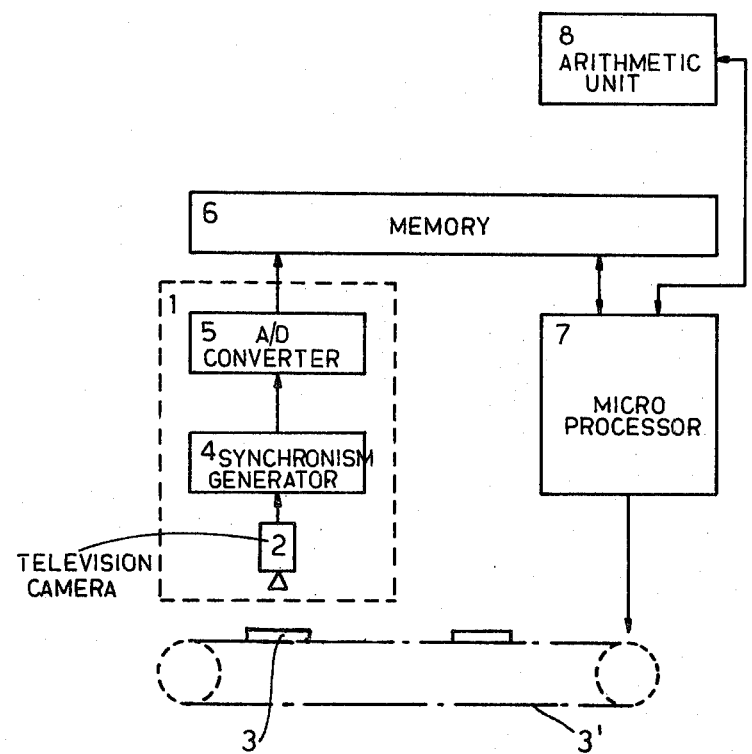
FIG. 1 is a block diagram of the apparatus according to the invention.

In FIG. 1 the dashed block 1 designates a general purpose apparatus for the reading and division or subdividing the image into dots, for each of which a determined value of an analog luminance level signals is obtained; in the specific case the above mentioned reading apparatus is a black and white television camera 2, such as a commercially available one according to CCIR standard with external synchronization, in front of which either the object 3 to be checked or the sample are placed.

The television camera 2 takes the image of the object 3 located on a general handling apparatus 3' and translates the information into analog signals that are supplied to block 4 for amplification and synchronism generation (synchronism generator commercially available at the CCIR standard with H, V, A, S signals); this generator, in addition to supplying all of the required synchronism to the television camera, provides for signal amplification.

The analog signal corresponding to the luminance level of each dot is supplied to an analog-digital converter 5 (Datel mod. ADV TV 8B) which converts the analog signal into 6-bit digital values, supplying it to frame memory 6.

As above described, the reading device 2 is black and white television camera, but which in the application, may be replaced by any reading device more appropriate to the handling system of the object to be checked, such as for example a single dot image scanning system with a photo multiplier for the sensing of a single dot or a sensing system with a silicon photodiode bar or a solid state television camera.

For the sensing of the coloured image, the black and white television camera 2 can be replaced by a color television camera or by a plurality of black and white television cameras provided with suitable filter for the scanning of the image into its fundamental chromatic components: in this case the analog signal may be divided and sequentially converted (one colour after the other) or in parallel for higher speeds by a multiplication of block 5.

The digital signal representing the luminance value of each dot coming out of block 5 is supplied to frame memory 6 storing the values relating to the individual dots according to the sensing sequence thereof, which are therefore stored together with the coordinates of the dot and then retrievable at any instant according to the storing sequence or in a programmable manner.

A frame memory 6 for containing, for example, a matrix of 512×512 dots is manufactured by TASCO S.p.A.—Milan, but it is available at other firms, such as Colorado Video Inc., Boulter, Colo. U.S.A.

In FIG. 1, block 7 is a controller or processor which is connected at one side to frame memory 6 and at the other to an arithmetic unit 8; this controller device 7 may be a microprocessor for intance a ZYLOG Z 80 manufactured by MOSTEK Corp. Texas—U.S.A. model OEM 80/4CPU with memory RAM 80 A×48 K byytes by the same firm.

The controller device 7 controls the frame memory 6 by reading the dots in the programmed sequence, supplying the same to the arithmetic unit 8 for the calculations to be hereinafter described in details, receiving the results therefrom and processing the signals relating to the object to be checked, for the operator or for the mechanical handling or selecting device.

Figure 2:
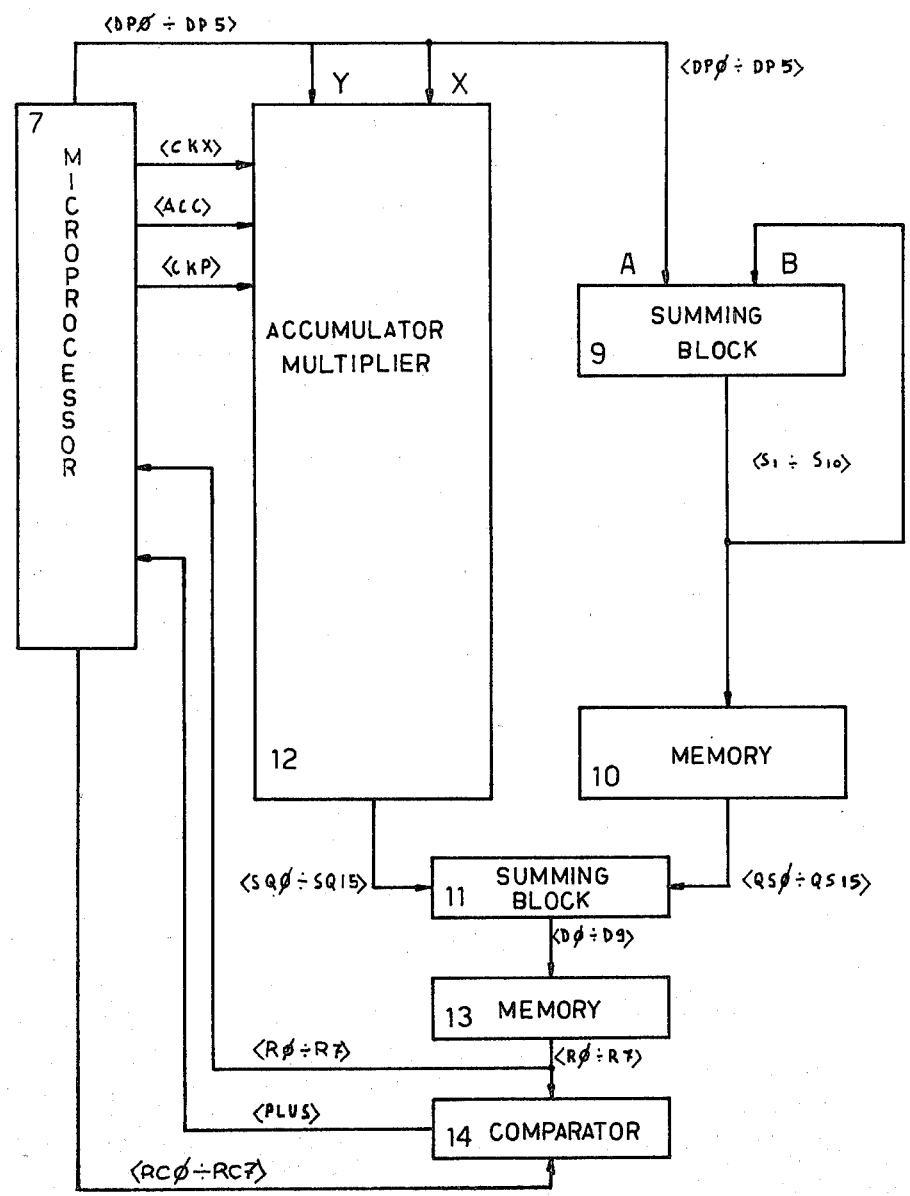
FIG. 2 is a block diagram of the arithmetic unit for calculating the the standard deviation for the sample and objects to be checked and comparison of the standard deviation relating to the same area.
Figure 4:
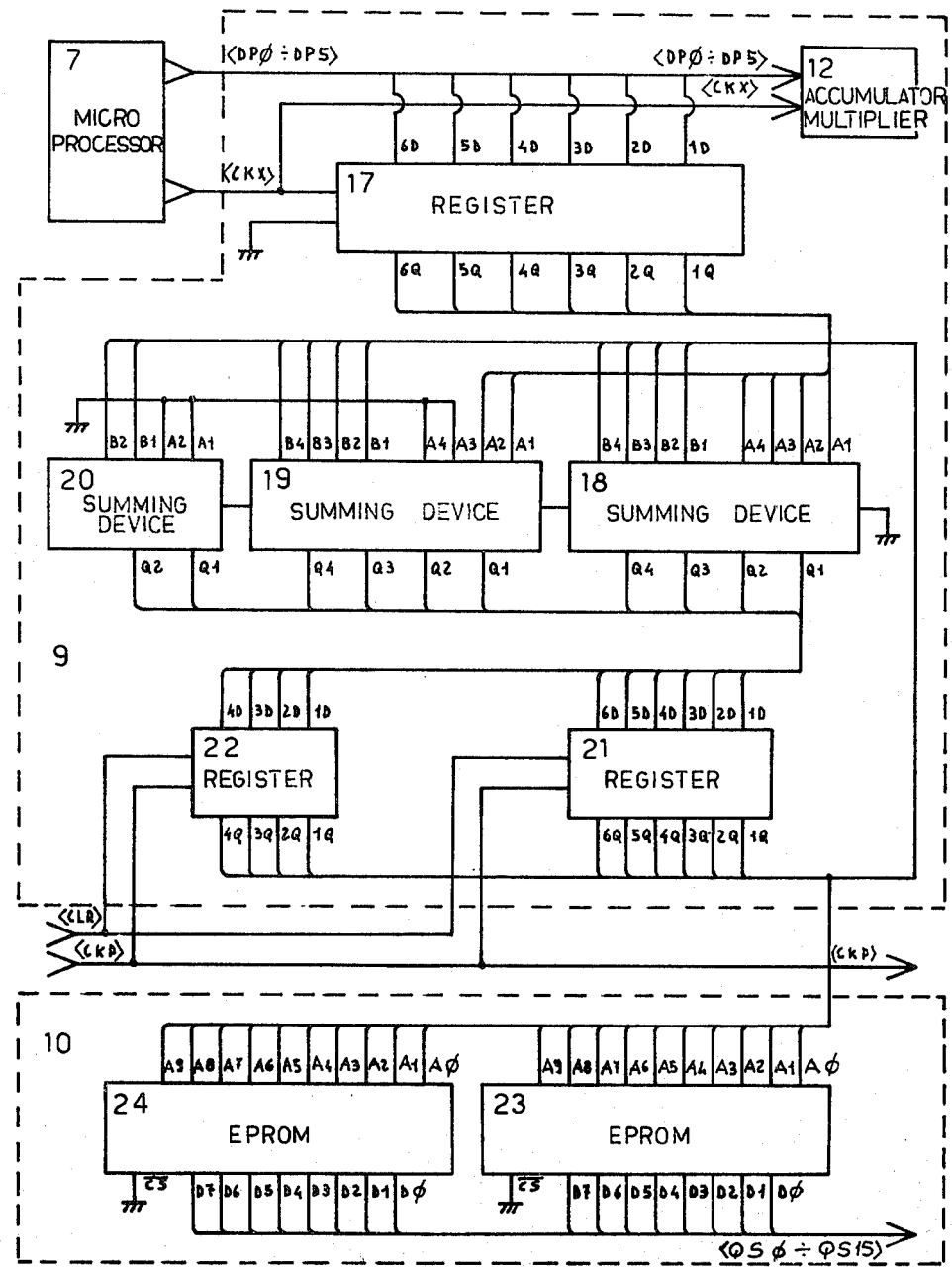
FIGS. 4 and 5 are the detailed block diagrams of the arithmetic unit outlined in FIG. 2.
Figure 5:
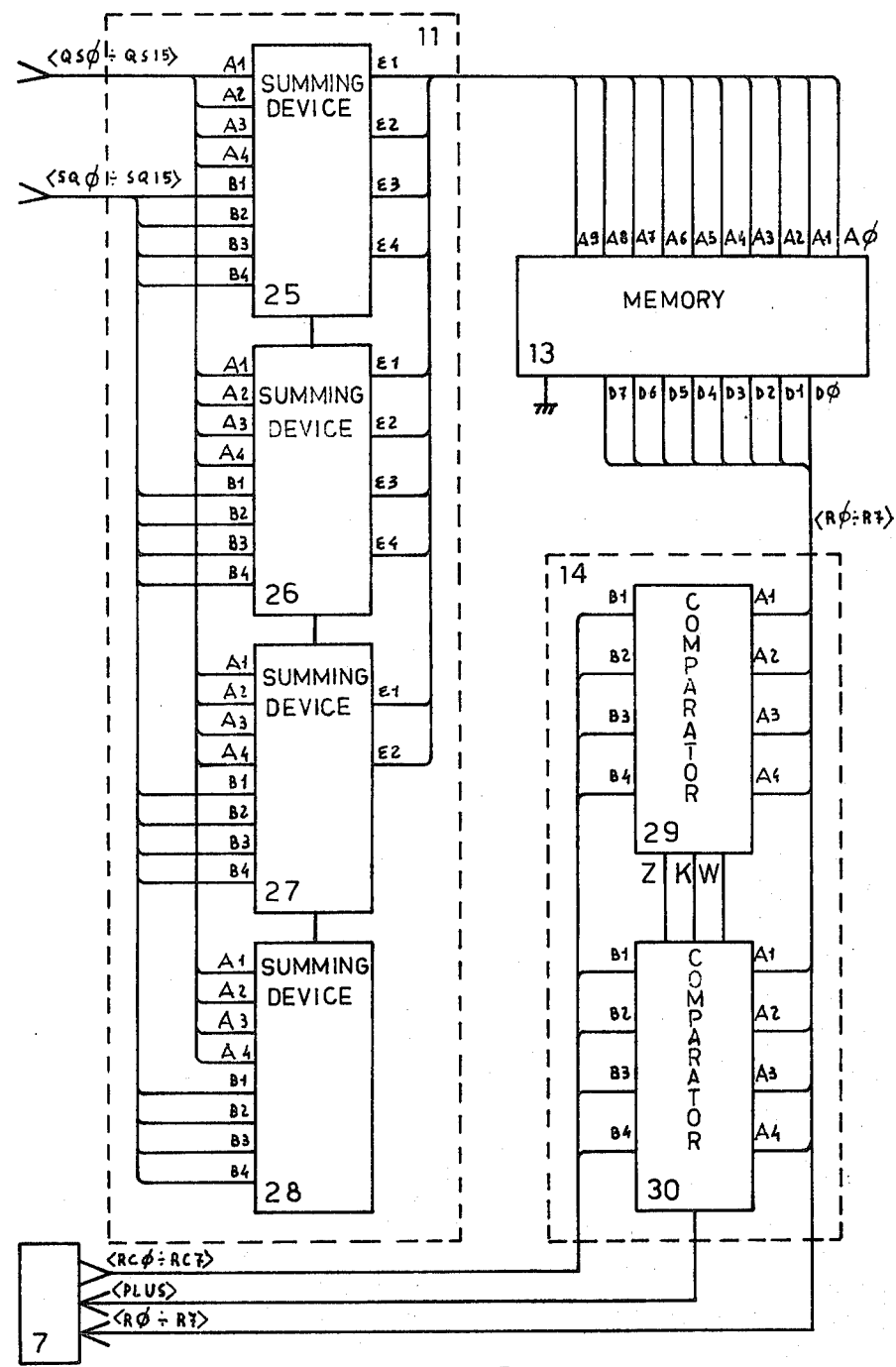

The calculating device 7 is programmed to read, in the frame memory 6, the dots of the stored image, of square matrixes of different sizes, i.e., in the above example, square areas of 4 dots by 4 dots or 16 dots per area for a total of 16.384 areas; the device 7 supplies the numerical value of the first dot from the first area to the arithmetic unit 8, the block diagram of which is shown in FIG. 2, while the detailed description of the blocks is shown in FIGS. 4 and 5.

The arithmetic unit 8 outlined in FIG. 2 calculates in real time the the standard deviation of the luminance values according to the formula:

$$\sigma = \sqrt{\frac{\sum\limits_{i=1}^{n} x_i^2}{n} - \frac{\left(\sum\limits_{i=1}^{n} x_i\right)^2}{n^2}}$$

and then compares the $\sigma$ values of said area between the sample and the object to be checked. The input datum from the calculating device 7 is a 6 bit numerical value $x_i$ of the dot represented by the signals $<DP0 \div DP5>$ in the sequence of the 16 dots of the area. On one hand to obtain $$\frac{\left(\sum\limits_{i=1}^{n} x_i\right)}{n^2},$$

the luminance value $x_i$ of each dot is supplied to the summing block 9 for the sum of the 16 dots: the result, which is represented by the signals $<S1 \div S10>$, and is a 10 bit number as a sum of 16 6-bit numbers, is supplied to block 10 which calculates the square thereof, dividing it by $n^2$ (that is to say 256) and puts it in 1's complement format, namely calculating the negative value thereof.

The result of this operation at the output of block 10 is supplied as a signal $<QS0 \div QS15>$ to summing block 11.

The input datum $<DP0 \div DP5>$ is simultaneously supplied to the two input groups x and y of block 12 for the calculation of the other term $$\frac{\sum\limits_{i=1}^{n} x_i^2}{n}.$$

Block 12, as a matter of fact, receives as an input twice the same numerical value of the dot, then multiples each other, that is to say calculates the square value thereof, sequentially adds the square values and divides the result by the number n of dots, namely 16 in the present example.

The output datum $<SQ0 \div SQ15>$ is supplied to the summing block 11 in order to subtract therefrom the value $<QS0 \div QS15>$ coming from block 10. The output of block 11 is the result of the difference (the variance), that is a 10 bit signal $<D0 \div D9>$ (the 10 bit difference coming out of block 11 is the result of the removal of the least significant 4 bits for next reduction of the calculation).

The signal $<D0 \div D9>$ is supplied to block 13 which estimates the last stage of the calculation for the standard deviation, that is to say the square root of the difference or variance.

The result at the output of block 13, namely $<R0 \div R7>$ is supplied to the controller device 7 contemporaneously to the comparator 14 comparing the value of the standard deviation for the object to be checked with the standard deviation $<RC0 \div RC7>$ from the calculating device 7 and relating to the corresponding area of the sample object.

The comparator will output a positve signal $<PLUS>$ to the calculating device 7 when $<R0 \div R7>$ is greater than $<RC0 \div RC7>$.

When the arithmetic unit 8 is processing the dots of an area of the sample, the device 7 supplies signals $<RC0 \div RC7>$ equal to 0 to the comparator; at this time the output signal from the comparator will be always $<PLUS>$ and the output result from block 13 $<R0 \div R7>$ will be stored by controller device 7.

On the other hand, when the arithmetic unit 8 is operating on the image of the object to be checked the controller device 7 supplies through $<RC0 \div RC7>$ the corresponding values of the sample and the comparator 14 will provide positive differences with signal $<PLUS>$ only where the object to be checked has greater values than the sample; however, the signals $<RC0 \div RC7>$ supplied from device 7, may be either the standard deviation calculated over the sample, or an adjusted value obtained by adding or multiplying a predetermined factor to the standard deviation.

The controller device will utilize these positive values as fault signals indicating a fault in the object.

We have schematically described the calculation process carried out by the arithmetic unit 8; and the result of such a transformation of the sample image into the standard deviation referred to small areas is stored into the calculating device 7: this new sample image which is transformed into $\sigma$ values (and no longer into luminance values) can be defined as an image of the object variability: that is to say no longer the image in its normal shape or as commonly seen, but represented by its standard deviations.

To numerical values $\sigma=0$ a fully uniform area would correspond, that is to say without any differences from dot to dot, whatever may be the luminance value of said area; at maximum values of $\sigma$, an extremely contrasted area would instead correspond, that is to say an "edge" area, which has half white dots and half black dots.

Figure 3A:
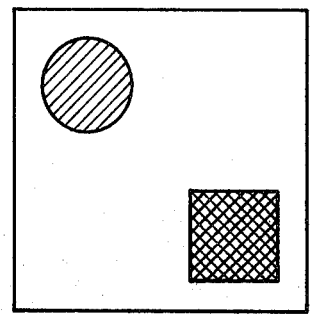
FIGS. 3A and 3B are a graphic exemplification of the image transformation carried out on a decorated tile.
Figure 3B:
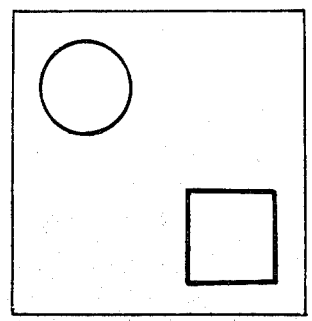

This transformation is schematically represented in FIGS. 3A and 3B, where FIG. 3A represents a normally white tile with a round grey drawing and a square black drawing.

On the other hand FIG. 3B represents the same tile transformed according to the above formula, which in this case will have a standard deviation equal to 0 over the whole white portion of the tile, and higher values of σ on the three edges: tile edge, circumference of the round drawing and perimeter of the square.

The controller device 7 stores the parameters of the sample image and is programmed to multiply them, for instance by a multiplying or adding factor, for causing the values of the parameters to be increased until the desired tolerance is obtained; that is, to provide that the difference, as calculated by comparator 14, with the object to be checked, is positive only when the object to be checked actually has a contrast that implies the presence of a fault.

This multiplying factor (or adding factor) is experimentally determined according to the type of objects to be checked, the characteristic of the faults, and also according to the lighting type and reading apparatus.

The controller device 7 is also programmed to add to one another all of the values of positive difference, or only the adjacent values, so as to eliminate the small casual differences and transmit different fault signals to the selecting and handling device according to the fault magnitude (difference value) and fault size (value of the difference sum).

In FIGS. 4 and 5 the detailed block diagram of the arithmetic unit 8 outlined in FIG. 2 is represented.

In FIG. 4, blocks 9 and 10 of FIG. 2 are shown: to calculate the sum schematically represented in block 9, the signals $DP\emptyset \div DP5$ of the first in-coming dot from controller device 7 are transferred to the inputs $<1D \div 6D>$ of register 17 (74 LS 374 circuit) and, on the leading edge of a clock or synchronizing signal CKX from calculating device 7, are transferred to the outputs $<1Q \div 6Q>$ of register 17, where they will remain until the leading edge of the next signal $<CKX>$.

Upon the appearance of this last signal, the data, present at outputs $<1Q \div 6Q>$ of register 17, are transmitted to inputs $<A1 \div A4>$, more simply referred to as inputs A of summing devices 18, 19 and 20 (summing devices 7483); said summing devices 18, 19 and 20 add the values present at inputs A to the values present at inputs B which, at this first stage, are still equal to 0.

The result of this first sum, present at the outputs Q of the above mentioned summing device, (18, 19, and 20) is supplied to inputs D of registers 21 and 22 (registers 74.174) and, on the leading edge of signal $<CKP>$ from calculating device 7 are then transferred to the outputs Q; this datum, which is the result of the first sum, is supplied to inputs B of the summing devices 18, 19 and 20, as outlined in FIG. 4.

The numerical information of the second dot $DP\emptyset \div DP5$ at the arrival of a new signal $<CKX>$ will be again supplied to inputs A of summing devices 18, 19 and 20 and added to the values of the first dot now present at inputs B of said summing devices, which devices will compute the second sum which is again stored in registers 21 and 22 which, at the leading edge of the next signal $<CKP>$ will allow the transfer thereof to inputs B of summing devices 18, 19 and 20.

This adding operation is repeated 16 times for the 16 dots of the involved area (generally n times) and, at the end of the 16 additions, in the registers 21 and 22, the summation of the 16 dots will appear (ε); this summation, at the signal $<CLR>$ from calculating device 7 (which clears the summing devices in readiness for the next area of 16 dots), is supplied to memories 23 and 24 (memories EPROM 2708) which are shown in FIG. 2 by block 10.

These memories 23 and 24 are programmable and contain, in this embodiment, some tables in which, at each address presented to their inputs A, corresponds at outputs D a value, equal to the square of said value divided by $n^2$ (256 in the case being examined) and complemented to 1: the outputs D of memories 23 and 24 are then the second term of the formula under square root, already made negative, and is supplied as signal $<QS\emptyset \div QS15>$ to the summing device 11 to be described below.

FIG. 2 shows block 12 comprising an accumulator multiplier (TRW-TDC 1010 J).

The signal $<DP\emptyset \div DP5>$ relating to the n dots of the involved area is supplied to inputs X and Y. In said multiplier 12, the data $<DP\emptyset \div DP5>$, contemporaneously present at said inputs X and Y, are multiplied to one another at the arrival of signal CKX from calculating device 7; the result is added to the dots which were already present at the arrival of signal ACC from calculating device 7 which, for the first dot, is equal to 0 and therefore does not cause any addition and, for the next 15 dots, is equal to 1 and causes the addition thereof to the preceding sum.

At the signal $<CKP>$ this sum is stored in the output register of multiplier 12 and, at the 16th or last signal, the result is presented to the 16 outputs of said multiplier for supply as signal $<SQ\emptyset \div SQ15>$ to the inputs B of the set of four summing devices 25, 26, 27 and 28 (summing devices 7483), see FIG. 5, forming the summing block 11 of FIG. 2; as it will be seen from FIG. 5, each summing device supplies to the next summing device a CARRY signal which can be a logical level 0 or 1 depending on whether or not the input bits overflow the summing device capacity, with the exception of the last summing device in the set, in which the CARRY signal is always at level 1, because of the required complement of the output sum.

In FIG. 5 the inputs A of the summing devices 25, 26, 27 and 28 receive the signal $<QS\emptyset \div QS15>$ from memories 23 and 24 of FIG. 4 and the inputs B of said summing devices receive the signal $<SQ\emptyset \div SQ15>$ from multiplier 12.

Taking into account that $QS\emptyset \div QS15$ is already a negative datum, the result of summing devices 25, 26, 27 and 28 is the difference under square root of the preceding formula. Only the most significant outputs (10 in the case being examined) of this result are connected to block 13 (memory EPROM 2708).

Also this memory is a programmable memory which in this case contains a table, so that upon presentation of the difference result to the inputs A $<D\emptyset \div D9>$, the datum at the outputs $<R\emptyset \div R7>$ is the square root of said result. If desired, the table could also be programmed to provide the square root logarithm.

The comparator block 14 of FIG. 2 is shown in greater detail in FIG. 5, in which the blocks 29 and 30 are comparators 74S85.

The inputs A of the two comparators 29 and 30 are presented with the results $<R\emptyset \div R7>$ of block 13; to the inputs B of said comparators the calculating device 7 supplies the data $<RC\emptyset \div RC7>$ relating to the sample, for the same area on which the calculation has been carried out.

The comparator 29 receiving at inputs A and at inputs B the most significants bits of the information, supplies to the second comparator 30 one of the following three signals:

Z if the number at inputs A is greater than that at inputs B;
W if the number at inputs B is greater than that at inputs A;
K if they are equal.

The comparator 30, receiving the least significant data of the information and the above described signals will supply the signal <PLUS> if <R0÷R7> is greater than <RC0÷RC7> as initially referred to.

What I claim is:

1. A method for detection of object faults, in real time, and comprising the steps of:
   scanning an object to be checked and detecting luminance levels of each of a finite number of dots thereof to provide analog image signals corresponding to each dot and indicative of said luminance levels;
   converting said analog signals to corresponding digital signals according to a luminance level scale and storing said digital signals in a memory to provide a digitized object image;
   dividing said digitized object image into a predetermined number of areas having a predetermined number of said dots;
   calculating standard deviations for digitized luminance values of the dots of each area into which the digitized object image has been divided according to the formula:

$$\sigma = \sqrt{\frac{\sum\limits_{i=1}^{n} x_i^2}{n} - \frac{\left(\sum\limits_{i=1}^{n} x_i\right)^2}{n^2}}$$

wherein:
   $x_1$ = luminance value of the individual dots pertaining to an area, and
   n = number of dots in the area;
   storing said standard deviations of said areas;
   providing digitized reference standard deviation values corresponding to each of said areas;
   comparing each of said standard deviations with said corresponding digitized reference standard deviation values; and
   providing a fault signal when a threshold is exceeded during said comparing.

2. A method as in claim 1, wherein said digitized standard deviation reference values are obtained by performing the steps prior to said comparing step on a sample object.

3. A method according to claim 2, wherein each of said digitized standard deviation reference values are multiplied by a predetermined factor prior to said comparing.

4. A method as in claim 2, wherein each of said digitized standard deviation reference values are added to a predetermined factor prior to said comparing.

5. A method as in claim 2, and further comprising the step of:
   defining basic color components of said objects and repeating the above sequence of steps, in parallel, for each of said basic color components.

6. A method as in claim 2, and further comprising the step of:
   defining basic color components of said objects and repeating the above sequence of steps, in series, for each of said basic color components.

7. An apparatus for detection of object faults in real time, and comprising:
   means for scanning an object to be checked and detecting luminance levels of each of a finite number of dots thereof to provide analog image signals corresponding to each dot and indicative of said luminance levels;
   means for converting said analog signals to corresponding digital signals according to a luminance level scale and storing said digital signals in a memory to provide a digitized object image;
   means for dividing said digitized object image into a predetermined number of areas having a predetermined number of said dots;
   means for calculating standard deviations for digitized luminance values of the dots of each area into which the digitized object image has been divided according to the formula:

$$\sigma = \sqrt{\frac{\sum\limits_{i=1}^{n} x_i^2}{n} - \frac{\left(\sum\limits_{i=1}^{n} x_i\right)^2}{n^2}}$$

wherein:
   $x_1$ = digitized luminance value of the individual dots pertaining to an area, and
   n = number of dots in the area;
   means for storing said standard deviations of said areas;
   means for providing digitized reference standard deviation values corresponding to each of said areas;
   means for comparing each of said standard deviations with said corresponding digitized reference standard deviation values; and
   means for providing a fault signal when a threshold is exceeded during said comparing.

8. An apparatus as in claim 7, and further comprising:
   means for multiplying each of said digitized standard deviation reference values by a predetermined factor prior to said comparing.

9. An apparatus as in claim 7, and further comprising:
   means for adding a predetermined factor to each of said digitized standard deviation reference values prior to said comparing.

10. An apparatus as in claim 7, and further comprising:
    means for multiplying each digitized luminance value of a particular predetermined area by itself to obtain a squared digitized luminance value, summing said squared digitized luminance values of said particular predetermined area to provide a sum of squares, and dividing said sum of squares by a total number of dots in said particular predetermined area to provide a first factor;
    means for summing said digitized luminance values of the dots of said particular predetermined area to provide a sum of digitized luminance values, squaring said sum of digitized values and dividing a result thereof by the square of a total number of dots in said predetermined area to obtain a second factor, and operating on said second factor to provide a one's complement thereof;

means for summing said first factor and said one's complement of said second factor to provide a variance;

means for taking the square root of said variance to provide said standard deviation; and means for providing said fault signal to a controller when a threshold is exceeded such that faulty objects may be sorted from objects which are not faulty.

11. An apparatus as in claim 2, and further comprising:

means for resolving said object into fundamental chromatic components and performing said fault detection according to said fundamental components.

* * * * *